(12) United States Patent
Fattinger et al.

(10) Patent No.: US 9,267,933 B2
(45) Date of Patent: Feb. 23, 2016

(54) HANGING DROPLET PLATE

(75) Inventors: Christof Fattinger, Blauen (CH); Patrick Iaiza, Saint Louis (FR); Tom Kissling, Riehen (CH); Dieter Voegelin, Sissach (CH); Thomas Zumstein, Weil Am Rhein (DE); Claudia Mcginnis, Riehen (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 186 days.

(21) Appl. No.: 14/002,269

(22) PCT Filed: Mar. 2, 2012

(86) PCT No.: PCT/EP2012/053588
§ 371 (c)(1),
(2), (4) Date: Dec. 23, 2013

(87) PCT Pub. No.: WO2012/117083
PCT Pub. Date: Sep. 7, 2012

(65) Prior Publication Data
US 2014/0106395 A1   Apr. 17, 2014

(30) Foreign Application Priority Data

Mar. 3, 2011   (EP) ..................... 11156741

(51) Int. Cl.
*G01N 33/50* (2006.01)
*C12M 3/00* (2006.01)
*B01L 3/00* (2006.01)
*C12M 1/12* (2006.01)
*B01L 3/06* (2006.01)

(52) U.S. Cl.
CPC ........ *G01N 33/5014* (2013.01); *B01L 3/50853* (2013.01); *C12M 25/01* (2013.01); *B01L 3/06* (2013.01); *B01L 3/5088* (2013.01); *B01L 2300/047* (2013.01); *B01L 2300/0829* (2013.01)

(58) Field of Classification Search
CPC .......... B01L 2300/042; B01L 3/50853; B01L 3/5088; B01L 2300/0829; B01L 2300/047; C12M 23/12; C12M 25/01
See application file for complete search history.

(56) References Cited

FOREIGN PATENT DOCUMENTS

| DE | 103 62 002 B4 | 10/2006 |
|---|---|---|
| JP | 2001-502057 | 2/2001 |
| JP | 2009-050194 | 9/2010 |
| JP | 2004-254622 | 4/2012 |
| WO | WO 03/078700 A1 | 9/2003 |
| WO | WO 2008/123741 A1 | 10/2008 |
| WO | WO 2010/031194 A1 | 3/2010 |

OTHER PUBLICATIONS

DE 10362002 B4 English Abstract. accessed Jul. 21, 2015.*
International Search Report for International Application No. PCT/EP2012/053588, date of completion of report Oct. 11, 2012.
English Abstract of Application No. JP 2001-502057A.
English Abstract of Application No. JP 2004-254622; JP4892181B2.
English Abstract of Application No. JP 2009-050194; JP2010-202585A.

* cited by examiner

*Primary Examiner* — Thaian N Ton
*Assistant Examiner* — Titilayo Moloye
(74) *Attorney, Agent, or Firm* — Mintz Levin Cohn Ferris Glovsky and Popeo, P.C.

(57) ABSTRACT

A hanging droplet plate (1) comprises a predetermined number of droplet compartments (10) each being capable of receiving a droplet of a liquid. The respective droplet compartment (10) comprises a circumferential microfluidic wetting barrier (102) which is arranged to surround a respective cavity (100) and which prevents a droplet from spreading beyond the microfluidic wetting barrier (102). The respective compartment (10) comprises a closed bottom (101) and at least one additional circumferential microfluidic wetting barrier (104), each additional circumferential microfluidic wetting barrier (104) which is arranged to surround a preceding circumferential microfluidic wetting barrier (102). A wettable area (103) is arranged between two adjacently arranged microfluidic wetting barriers (102, 104).

15 Claims, 14 Drawing Sheets

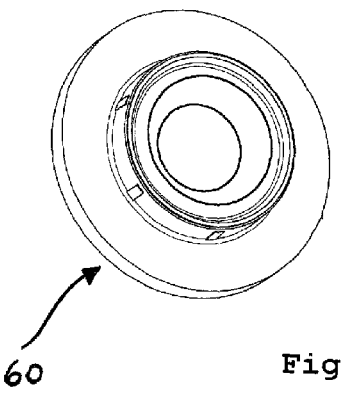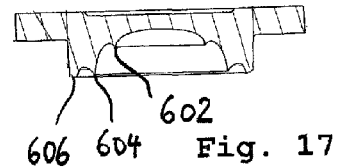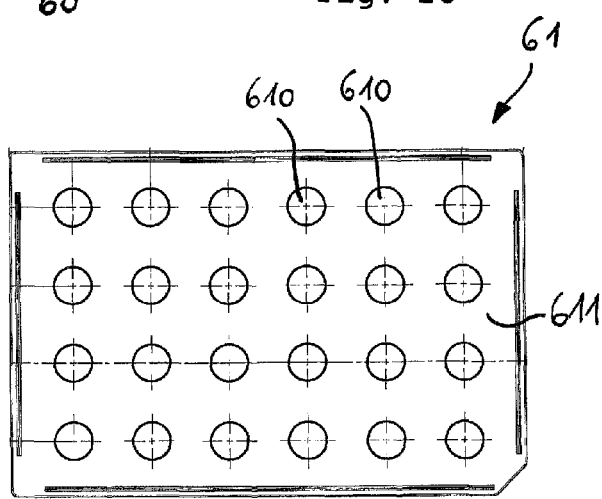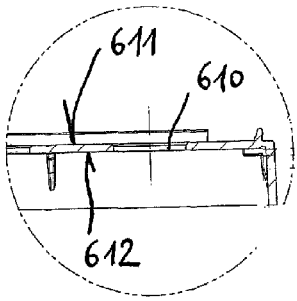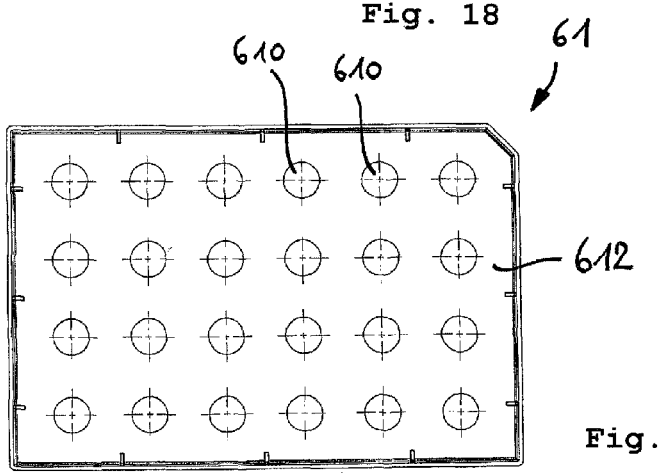

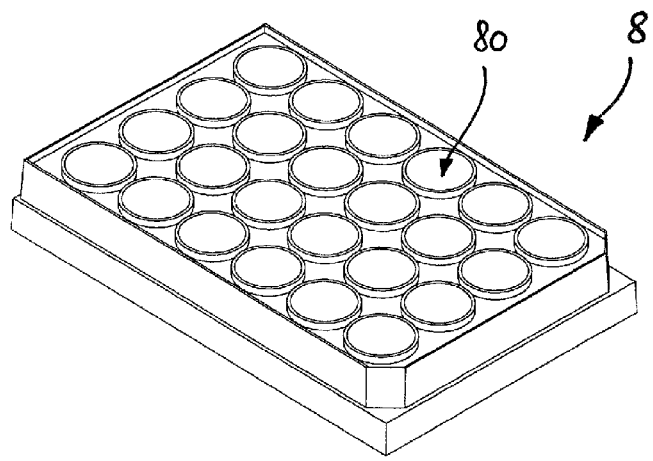
Fig. 25
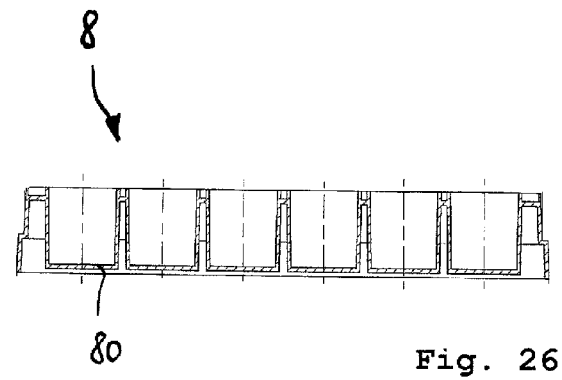
Fig. 26
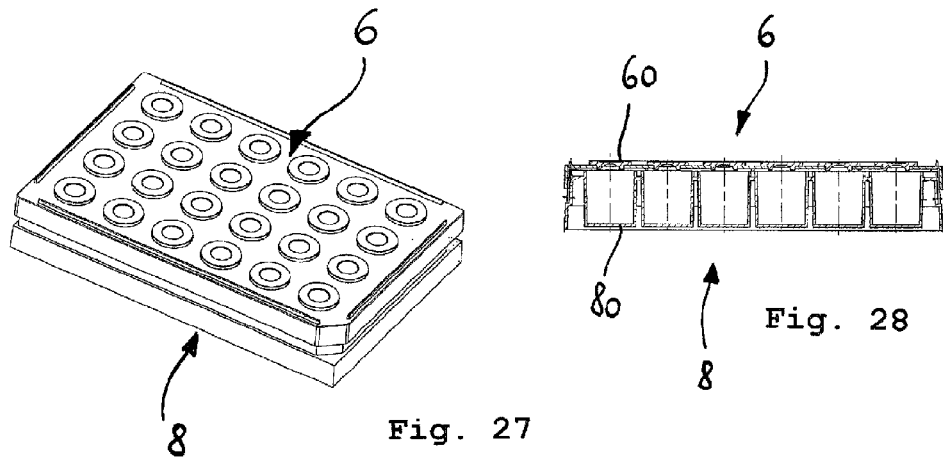
Fig. 27
Fig. 28

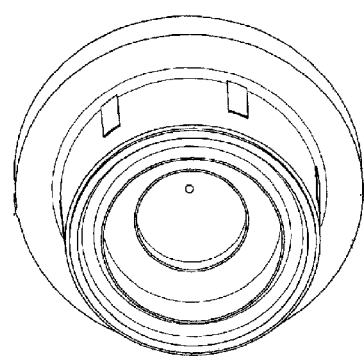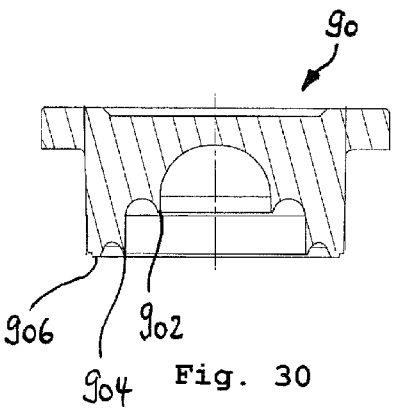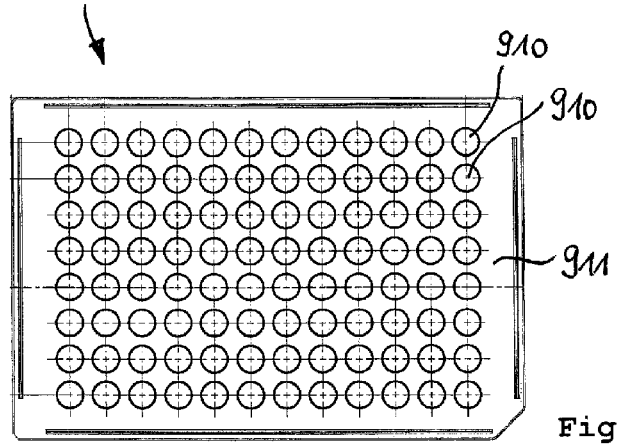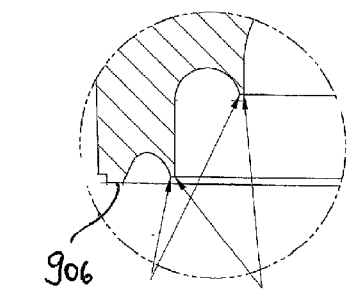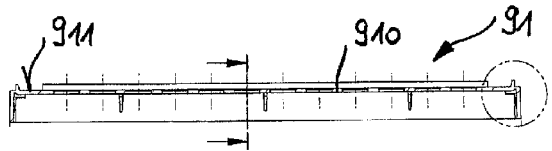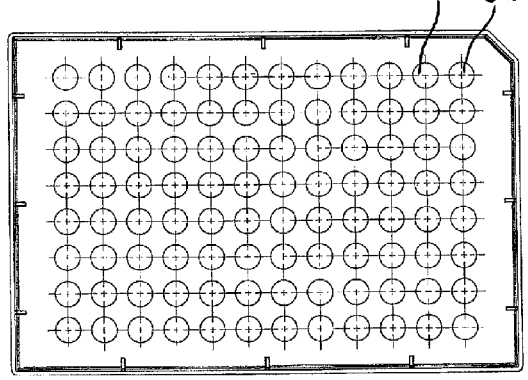

HANGING DROPLET PLATE

CROSS REFERENCE TO RELATED APPLICATIONS

The present application is a 35 U.S.C. 371 national stage entry of PCT/EP2012/053588, which has an international filing date of Mar. 2, 2012 and claims priority to European Patent Application No. 11156741.8, filed on Mar. 3, 2011. The present application incorporates herein by reference the disclosures of each of the above-referenced applications in their entireties.

The present invention relates to a hanging droplet plate in accordance with the independent claim.

It is generally accepted that cells cultured in a three-dimensional configuration are physiologically more relevant than cells in classical two-dimensional (monolayer) cultures in a number of applications and assays, for example in drug discovery or in toxicity assays. Hanging droplet plates have been suggested to form such three-dimensional cellular aggregates. Drops of cell culture medium with suspended cells are placed into a culture compartment or well of such plate and the plate is then inverted. As there is no substrate available to which the cells can adhere, they accumulate at the apex of the hanging droplet and form a three-dimensional cellular aggregate. In case embryonic stem cells are used, these stem cells sink to the apex of the droplet where they meet to form the three-dimensional cellular aggregate, referred to as embryoid body.

A hanging droplet plate dispensing with the necessity to invert the plate is shown in WO 2010/031194. The plate shown in this reference comprises a plate body, first and second coplanar surfaces and a plurality of conduits penetrating the entire body perpendicularly from the first (upper) surface to the second (lower) surface. The conduit comprises a funnel-shaped inlet compartment close to the first (upper) surface, an inverted funnel-shaped culture compartment close to the second (lower) surface, and a capillary portion arranged between the inlet compartment and the culturing compartment. Relief structures in the form of individual rims protruding from the second (lower) surface of the body and surrounding each culturing compartment are provided. These rims prevent the liquid droplets from spreading beyond the rims.

Introduction of the liquid containing the cells into the culture compartment is performed through the inlet compartment and the capillary portion. By way of example, a liquid culture medium containing stem cells can be introduced in this manner into the culture compartments and the plate with the hanging droplets can then be incubated for a predetermined time interval so that the cells aggregate to form three-dimensional embryoid bodies. In case fresh liquid culture medium must be supplied after some time, this is performed by aspirating "old" liquid culture medium through the inlet compartment and the capillary portion (e.g. with the aid of a pipette) and then supplying "fresh" liquid culture medium in the manner described above.

While the plate described in WO 2010/031194 is generally suitable for culturing cells to form three-dimensional cellular aggregates, it offers space for improvement. For example, in order to aspirate old liquid culture medium through the inlet compartment and the capillary portion, an aspirating device (e.g. a pipette) is needed which must be embodied to tightly fit against the walls of the inlet compartment to effect proper aspiration. The same holds for the subsequent supply of fresh liquid culture medium. However, more importantly the stability of the hanging droplet in the respective culture compartment is only limited. Another disadvantage is that liquid may evaporate through the open inlet compartment at an uncontrolled rate.

Therefore, it is an object of the invention to suggest a hanging droplet plate which overcomes the afore-mentioned problems related to the stability of the hanging droplets and the evaporation of liquid. Also, additional supply or replacement of liquid culture medium should be easy to perform.

To achieve the afore-mentioned object(s), the present invention suggests a hanging droplet plate as it is specified by the features of the independent claim directed to such hanging droplet plate. Further embodiments of the hanging droplet plate according to the invention are the subject of the dependent claims.

In particular, the invention suggests a hanging droplet plate comprising a predetermined number of droplet compartments each being capable of receiving a droplet of a liquid. The respective droplet compartment comprises a circumferential microfluidic wetting barrier arranged to surround a respective cavity and preventing a droplet from spreading beyond the microfluidic wetting barrier. Moreover, the respective compartment comprises a closed bottom and at least one additional circumferential microfluidic wetting barrier, each additional circumferential microfluidic wetting barrier being arranged to surround a preceding circumferential microfluidic wetting barrier, with a wettable area being arranged between two adjacently arranged microfluidic wetting barriers.

The closed bottom configuration of the culture compartments together with the circumferential wetting barrier serves for an improved stability of the droplets hanging down from the respective culture compartments, in particular when compared with the hanging droplet plate shown in WO 2010/031194, and this is believed to be due to the non-existing access for air in contrast to the hanging droplet plate of WO 2010/031194 where there is access for air at the inlet compartment. Also, due to the non-existing access to air evaporation of liquid is greatly reduced.

In addition, although the hanging droplet plate must be re-inverted to supply a droplet of an additional liquid culture medium to the droplet already contained in the culture compartment to form a larger droplet this can be performed in an easy and convenient manner. This is firstly due to the good droplet stability, and secondly this is due to the additional circumferential microfluidic wetting barrier and the wettable area between the additional microfluidic wetting barrier and the preceding microfluidic wetting barrier which allow the easy supply of an additional droplet of liquid culture medium. The so formed larger droplet is prevented from spreading out by the said additional microfluidic barrier, so that a good stability of the larger droplet is maintained after the plate is inverted again to the hanging droplet configuration. Generally, the number of additional microfluidic wetting barriers is not limited, however, in practical embodiments only one or two additional microfluidic wetting barriers may be present.

In one embodiment of the hanging droplet plate according to the invention the respective droplet compartments are wells, while in another embodiment the droplet compartments may be formed by a plane surface (surrounded by microfluidic wetting barriers, respectively).

In a further embodiment of the hanging droplet plate according to the invention, the circumferential microfluidic wetting barrier comprises a circumferential edge and the at least one additional circumferential microfluidic wetting barrier comprises at least one additional circumferential edge. Each additional circumferential edge being arranged to surround a preceding circumferential edge, with the wettable area being arranged between two adjacently arranged circumferential edges. In a further variant of this embodiment, two adjacent circumferential edges are arranged in a stepped manner.

In a further embodiment, the hanging droplet plate according to the invention is made of a separately manufactured plate having a predetermined number of holes therein and of a corresponding predetermined number of separately manufactured wells forming the droplet compartments, with each separately manufactured well being press-fitted into a respective hole of the separately manufactured plate. This allows for an easy manufacture of both the plate and the wells, which can be made from polystyrene or from any other suitable material. The separately manufactured plate and wells can be easily assembled by press-fitting the wells into the holes. While generally also ultrasonic welding of the wells to the inner surface of the plate is an option (in this case the plate may not comprise holes), press-fitting the wells into holes is preferred since ultrasonic welding may make the microscopic analysis of the contents contained in the wells more difficult.

In a further embodiment of the hanging droplet plate according to the invention, the separately manufactured wells are press-fitted into the holes from that side of the plate forming the outer surface of the plate. This allows for an easy assembly of the plate and the wells which may be performed automatically. In a preferred embodiment, the hanging droplet plate according to the invention may comprise a number of 24 wells, 96 wells or 384 wells.

In another embodiment of the hanging droplet plate according to the invention, the circumferential microfluidic wetting barrier comprises a circumferential rim and the at least one additional microfluidic wetting barrier comprises an additional circumferential rim, each additional circumferential rim surrounding a preceding circumferential rim, with the wettable area being arranged between two adjacently arranged circumferential rims. In one variant of this embodiment, the adjacently arranged circumferential rims are arranged in a stepped manner, while in another variant of this embodiment the circumferential rims are arranged on a plane surface.

A further aspect of the invention relates to a hanging droplet plate assembly comprising a hanging droplet plate according to the invention as it is described above and a receiving plate. The hanging droplet plate has a predetermined number of droplet compartments or wells, and the receiving plate has a number of wells corresponding to the predetermined number of droplet compartments or wells of the hanging droplet plate. The hanging droplet plate and the receiving plate are assembled in a manner such that in the assembled state the wells of the receiving plate are arranged aligned with the droplet compartments or wells of the hanging droplet plate. This assembly allows to easily transfer the three-dimensional cellular aggregates from the hanging droplet plate to the wells of the receiving plate through centrifugation of the assembly.

Another aspect of the invention relates to a method of testing a substance for its toxicity to cells. The method comprises the steps of:

a) introducing a predetermined number of liquid droplets into a corresponding number of culture compartments of a hanging droplet plate, each droplet containing a predetermined volume of the substance to be tested and of a liquid culture medium as well as a plurality of cells;

b) inverting and incubating the hanging droplet plate for a predetermined time interval with the hanging droplet plate carrying the droplets in a manner such that they hang down from the respective culture compartments to allow the cells to form three-dimensional cellular aggregates in the respective droplets, c) supplying additional liquid culture medium to the droplets in the culture compartments in the culture compartments to promote additional growing of the three-dimensional cellular aggregates; and d) analyzing the three-dimensional cellular aggregates in order to assess whether the substance to be tested is toxic to the three-dimensional cellular aggregates.

In the method according to the invention a hanging droplet plate according to the invention is used as it is described above, and step c) is performed by re-inverting the hanging droplet plate, adding a droplet of the additional liquid culture medium to the respective droplets containing the three-dimensional cellular aggregates so as to form respective larger droplets in the respective culture compartments. Then, the hanging droplet plate is inverted again to allow the three-dimensional cellular aggregates to grow in the respective larger droplets hanging down from the culture compartments. The advantages are already mentioned above when discussing the advantages of the hanging droplet plate according to the invention. In addition, it allows automatization of at least some of the process steps, e.g. the supplying of additional liquid culture medium.

One embodiment of the method according to the invention further comprises the steps of e) transferring the grown three-dimensional cellular aggregates from the culture compartments of the hanging droplet plate into a corresponding number of wells of a receiving plate;

f) incubating the receiving plate with the wells containing the three-dimensional cellular aggregates for a further predetermined time interval; and g) after incubation analyzing the three-dimensional cellular aggregates in order to assess whether the substance to be tested is toxic to the three-dimensional cellular aggregates.

In a preferred variant of this embodiment of the method according to the invention, step e) is performed by assembling the hanging droplet plate and the receiving plate in a manner such that the respective wells of the receiving plate are arranged opposite to the respective culture compartments of the hanging droplet plate, and subsequently centrifugation of the assembled plates is performed. This allows a convenient and automatic transfer of the three-dimensional cellular aggregates from the hanging droplet plate to the respective wells of the receiving plate.

In a further embodiment of the method according to the invention, the cells are embryonic stem cells and the three-dimensional cellular aggregates are embryoid bodies. The step of analyzing the three dimensional cellular aggregates to assess whether the substance to be tested is toxic to the three-dimensional cellular aggregates is performed by analyzing whether the embryoid bodies contain myocardial cells. This embodiment is convenient since the presence of myocardial cells in the three-dimensional cellular aggregates can be easily detected, since myocardial cells beat.

Further advantageous aspects of the invention will become apparent from the following detailed description of embodiments with the aid of the drawings in which:

FIG. 16 shows a separately manufactured well of an embodiment of a 24-well hanging droplet plate according to the invention in a perspective view;

FIG. 17 shows the well of FIG. 16 in a cross-sectional view;

FIG. 18 shows a top view of a separately manufactured plate of the embodiment of the 24-well hanging droplet plate according to the invention, into the holes of which the separately manufactured wells of FIG. 16 can be inserted;

FIG. 19 shows a bottom view of the plate of FIG. 18;

FIG. 20 shows an enlarged view of a detail of the plate of FIG. 18 and FIG. 19 including one of the holes into which the wells are to be inserted;

FIG. 25 shows a perspective view of an embodiment of a further 24-well plate to which the 24-well hanging droplet plate of FIG. 21 can be mounted (similar to the assembly shown in FIG. 15);

FIG. 26 shows a cross-sectional view of the embodiment of the further 24-well plate of FIG. 25;

FIG. 27 shows a perspective view of the 24-well hanging droplet plate of FIG. 21 mounted to the further 24-well plate shown in FIG. 25;

FIG. 28 shows a cross-sectional view of the plate assembly shown in FIG. 27;

FIG. 29 shows a separately manufactured well of an embodiment of a 96-well hanging droplet plate according to the invention in an enlarged perspective view;

FIG. 30 shows the well of FIG. 29 in a cross-sectional view;

FIG. 31 shows a detail of the well of FIG. 29 including the stepped circumferential rims forming the microfluidic wetting barriers;

FIG. 32 shows a top view of a separately manufactured plate of the embodiment of the 96-well hanging droplet plate according to the invention, into the holes of which the separately manufactured wells of FIG. 29 can be inserted;

FIG. 33 shows a cross-sectional view of the plate of FIG. 32 including the holes into which the wells of FIG. 29 can be inserted;

FIG. 34 shows a bottom view of the plate of FIG. 32;

Figure 35:
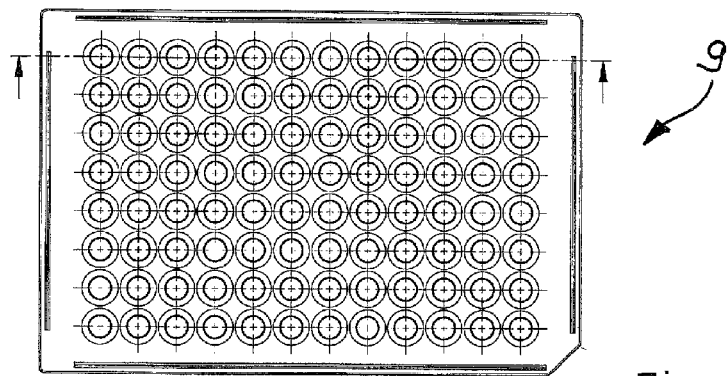
FIG. 35 shows a top view of the 96-well hanging droplet plate with the wells of FIG. 29 being inserted into the holes of the plate of FIG. 32.
Figure 36:
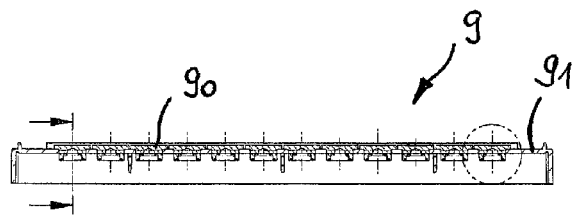
FIG. 36 shows a cross-section through the 96-well hanging droplet plate of FIG. 35.
Figures 37, 38:
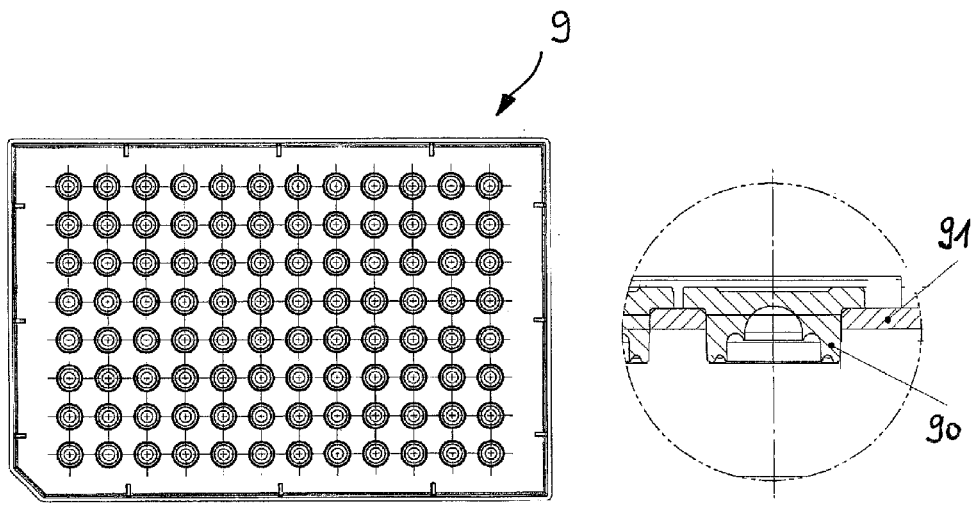
FIG. 37 shows a bottom view of the 96-well hanging droplet plate of FIG. 35.
FIG. 38 shows a detail of the cross-sectional view of FIG. 36 including one well inserted into one hole.
Figure 39:
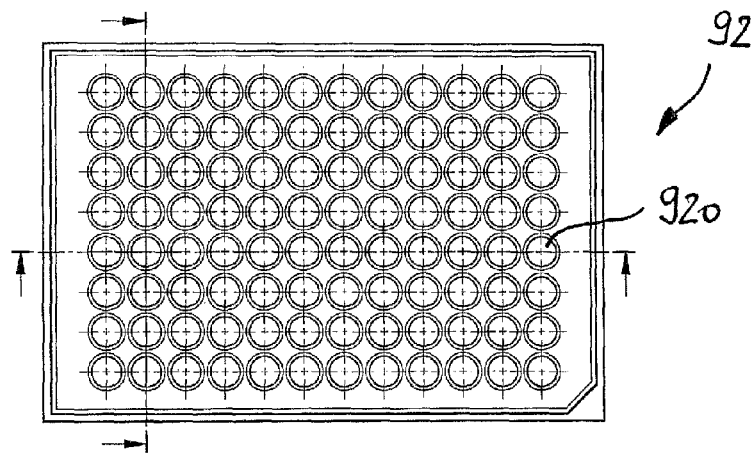
FIG. 39 shows a top view of an embodiment of a further 96-well plate to which the 96-well hanging droplet plate of FIG. 35 can be mounted (similar to the assembly shown in FIG. 15)
Figure 40:
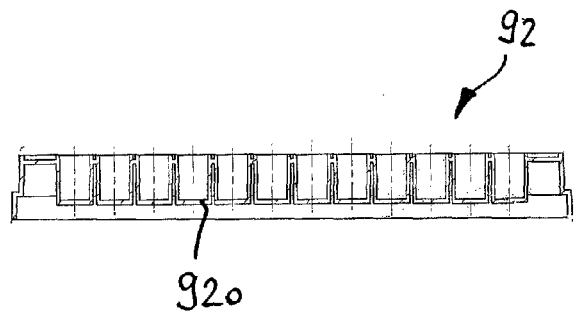
Figure 41:
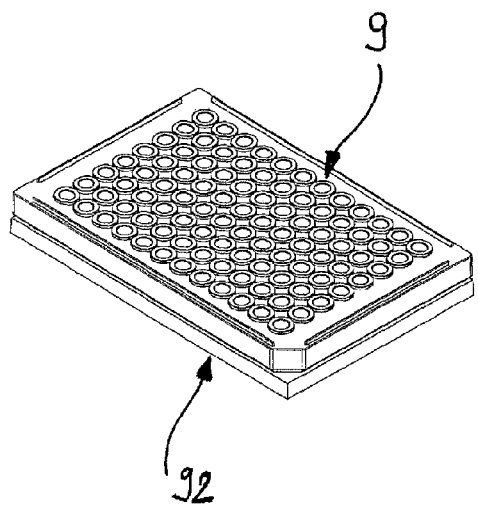

FIG. 40 shows a cross-sectional view of the embodiment of the further 96-well plate of FIG. 39; and FIG. 41 shows a perspective view of the 96-well hanging droplet plate of FIG. 35 mounted to the further 96-well plate shown in FIG. 39.

FIG. 1 to FIG. 6 show a first embodiment of a hanging droplet plate 1 according to the invention or details thereof in various views (see above). Plate 1 comprises a predetermined number of droplet compartments in the form of wells 10. The embodiment shown is a 24-well plate, however, any other number of wells is conceivable. Preferred are plates having a standardized number of wells which are arranged in accordance with standard microwell-plates, such as 96-well plates or 384-well plates.

Figure 6:
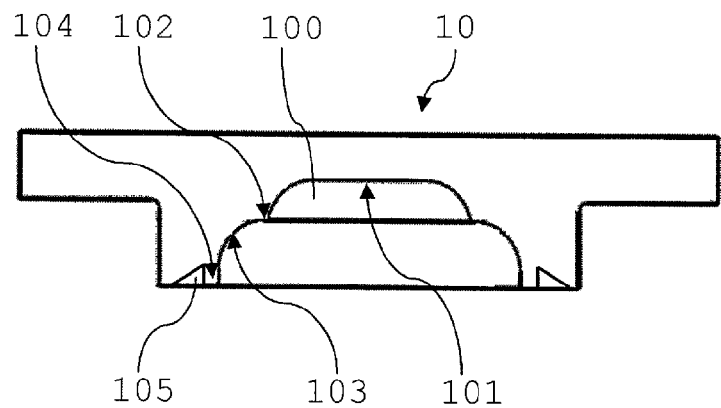
FIG. 6 shows an enlarged view of one well of the embodiment of the hanging droplet plate of FIG. 1.

While generally different embodiments of the wells are conceivable, the wells 10 of the embodiment of the hanging droplet plate 1 are embodied as is shown in an enlarged view in FIG. 6. Well 10 comprises a first circumferential wetting barrier in form of a sharp circumferential edge 102 surrounding a first cavity 100 having a closed bottom 101. First circumferential edge 102 is surrounded by a second sharp circumferential edge 104 with a wettable area 103 being arranged between first circumferential edge 102 and second circumferential edge. As can be seen in FIG. 6, the circumferential edges are arranged in a stepped manner, although this is not mandatory. An annular cut-out 105 is provided in a manner surrounding the second circumferential edge 104.

Figure 1:
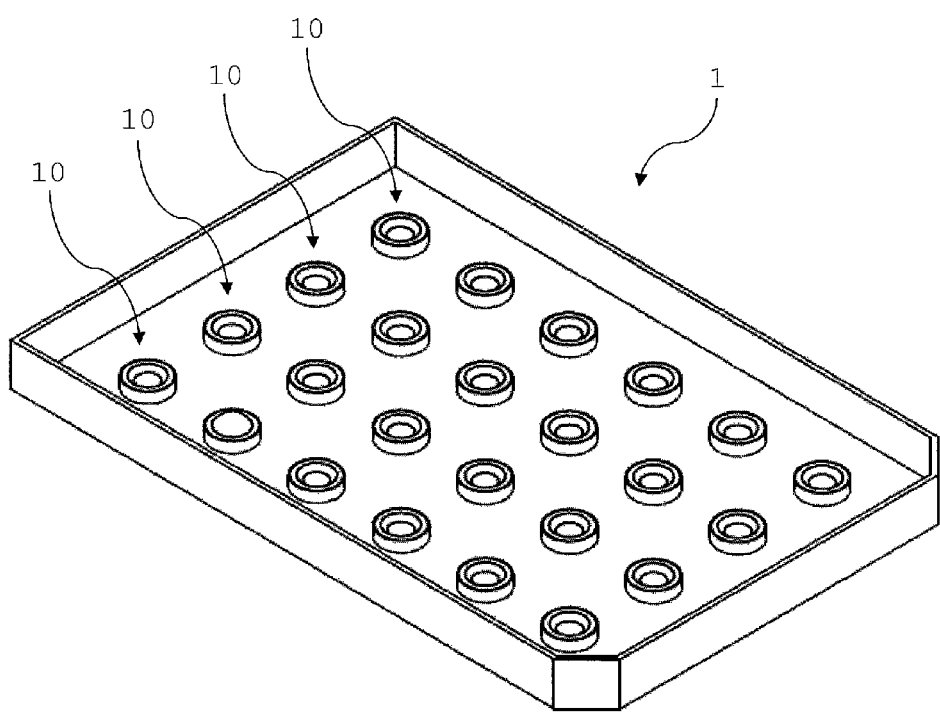
FIG. 1 shows a perspective view of a first embodiment of the hanging droplet plate according to the invention, with one well containing a droplet and with another well containing a droplet to which an additional droplet has been added.
Figure 2:
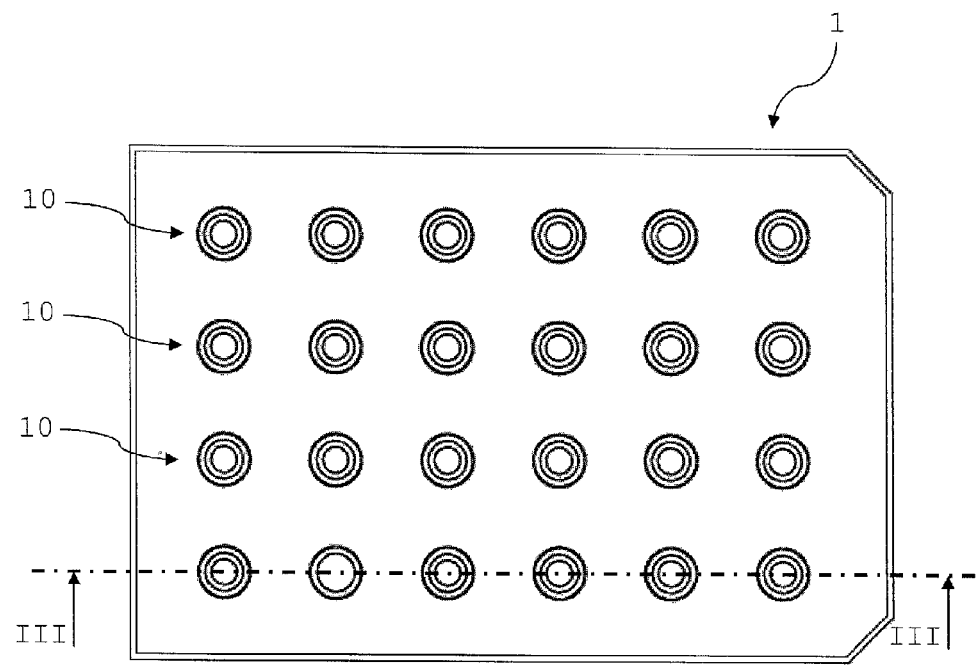
FIG. 2 shows a top view of the embodiment of the hanging droplet plate of FIG. 1.
Figure 3:
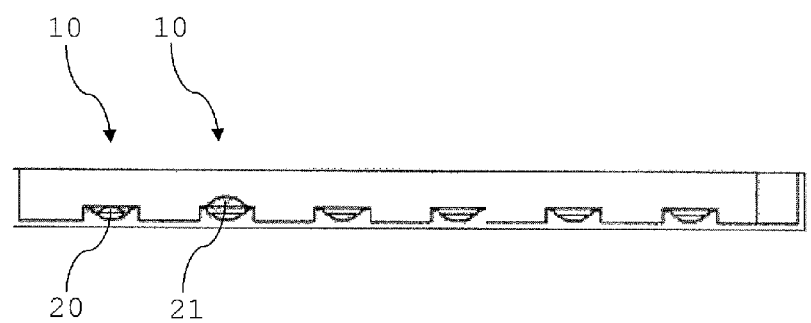
FIG. 3 shows a cross-sectional view along line III-III in FIG. 2 with the hanging droplet plate being re-inverted.
Figure 4:
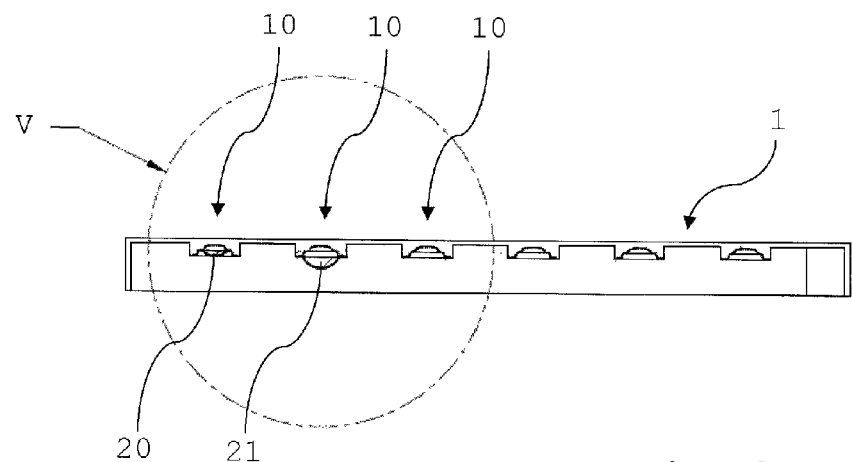
FIG. 4 shows a cross-sectional view along line III-III in FIG. 2 with the hanging droplet plate being inverted.
Figure 5:
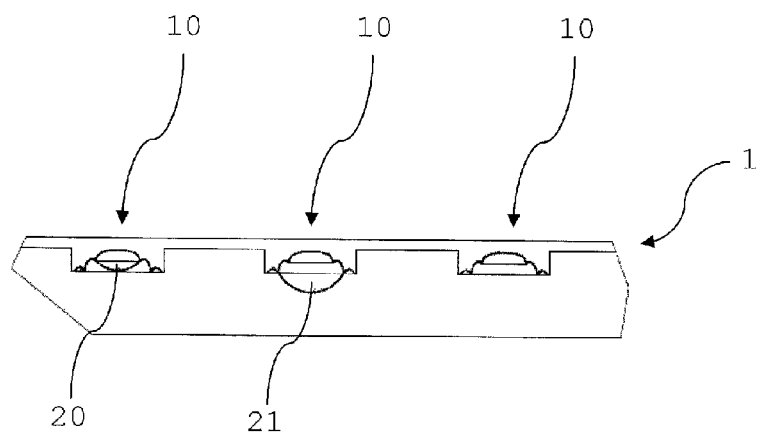
FIG. 5 shows an enlarged view of detail V of FIG. 4.

The reason for the geometric configuration of wells 10 is getting more clear when glancing at FIG. 3, FIG. 4 and FIG. 5 which represent the process of supplying droplets to the wells 10 and making them hang down from the wells 10. In FIG. 3 hanging droplet plate 1 is shown in re-inverted position, that is to say with the wells 10 facing upwardly. In that well 10 which is arranged at the outermost left position, a small liquid droplet 20 can be recognized. In the second well 10 from the left a larger droplet 21 can be recognized which has been obtained by having supplied another liquid droplet to the droplet 20 so as to form the larger droplet 21. It can be seen, that the supply of droplets to the wells 10 can be performed, for example, with the aid of a pipette. In particular, the placing of droplets into the wells 10 can be performed with the aid of a pipetting robot but can also be done manually. Also, in case some liquid is to be aspirated from a well (e.g. in case it is intended to replace an "old" liquid culture medium with "fresh" liquid culture medium) this can be easily performed as the droplets are easily accessible.

FIG. 4 shows hanging droplet plate 1 in the position in which the smaller droplet 20 and the larger droplet 21 hang down from the respective wells 10, and this can be seen best in FIG. 5 which shows detail V of FIG. 4. The smaller droplet 20 is hanging down from the outermost left well 10 whereas the larger droplet 21 is hanging down from the second well 10 from the left.

From FIG. 5 and FIG. 6 the function of the first and second circumferential edges 102 and 104 as microfluidic barriers preventing droplet 20 and larger droplet 21 from spreading beyond the edges is getting more clear. The first and second circumferential edges 102 and 104 thus contribute to stabilization of the droplet hanging down from the respective well 10. With respect to the second circumferential edge 104 this effect is enhanced through the annular cut-out 105. The wettable area 103 arranged between the first and second circumferential edges 102 and 104 (see FIG. 6) allows to easily add an additional liquid droplet to droplet 20 to form larger droplet 21 (see FIG. 4 and FIG. 5). The closed bottom 100 of wells 10 prevents liquid from evaporating through a hole or channel passing through the bottom and also serves to stabilize the droplets hanging down from the wells due to preventing air to push the droplet "from behind".

Figure 7:
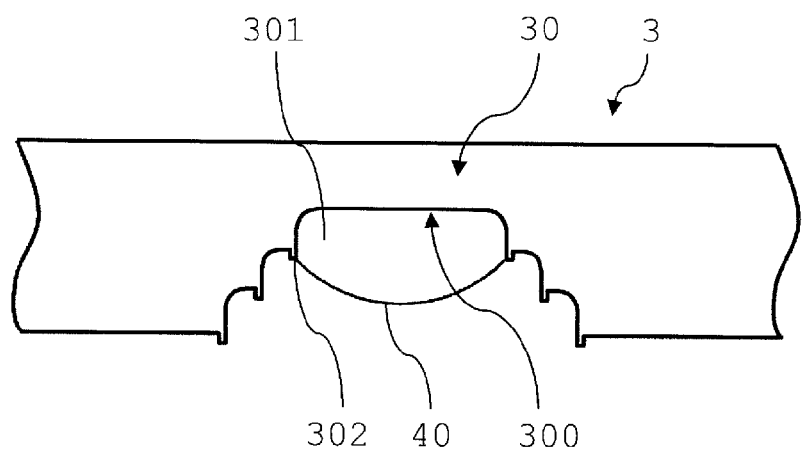
FIG. 7 shows a cross-sectional view of a well of a second embodiment of the hanging droplet plate according to the invention, the well containing a droplet.
Figure 8:
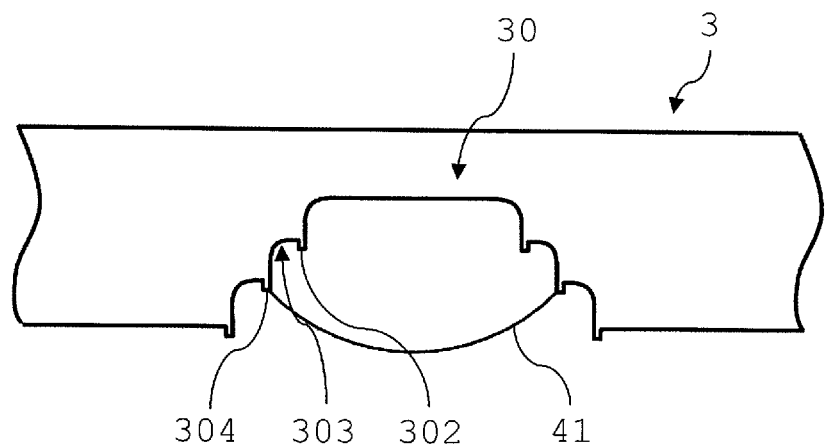
FIG. 8 shows the well of the second embodiment of the hanging droplet plate with an additional droplet having been added.
Figure 9:
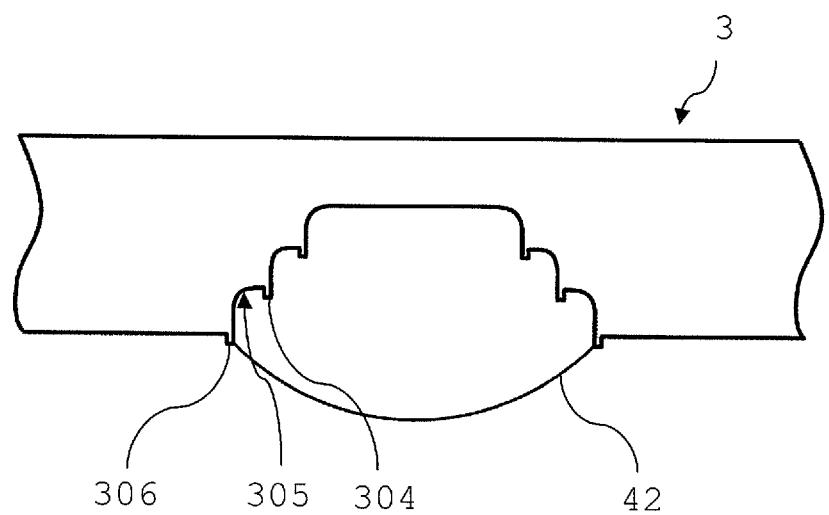
FIG. 9 shows the well of the second embodiment of the hanging droplet plate, with another additional droplet having been added.

A second embodiment of the hanging droplet plate according to the invention is shown in FIG. 7 to FIG. 9 in which only a single well 30 of the hanging droplet plate 3 is shown, respectively. This embodiment is somehow related to the first embodiment described in detail above in that it also comprises a stepped configuration of the microfluidic barriers preventing a droplet from spreading beyond the respective microfluidic barrier. However, the second embodiment is different from the first embodiment in that instead of the sharp edges the wells 30 comprise a cavity 301 having a closed bottom 300 which is surrounded by a first circumferential rim 302 surrounding cavity 301 and protruding beyond the cavity towards the open end of well 30. FIG. 7 shows a small liquid droplet 40 hanging down from well 30. Droplet 40 is retained in cavity 301 by the first circumferential rim 302 forming a microfluidic barrier.

FIG. 8 differs from FIG. 7 in that another liquid droplet has been added to liquid droplet 40 to form a larger droplet 41. Larger droplet 41 is retained by a second circumferential rim 304 surrounding the first circumferential rim 302 with a wetting area 303 being arranged between first circumferential rim 302 and second circumferential rim 304. Again, second circumferential rim 304 acts as a microfluidic barrier preventing larger droplet 41 from spreading beyond rim 304.

FIG. 9 differs from FIG. 8 in that still another liquid droplet has been added to larger droplet 41 to form an even larger droplet 42. Droplet 42 is retained by a third circumferential rim 306 surrounding the second circumferential rim 304 with another wetting area 305 being arranged between the second circumferential rim 304 and the third circumferential rim 306. Again, third circumferential rim 306 acts as a microfluidic barrier preventing the even larger droplet 42 from spreading beyond rim 306.

Figure 10:
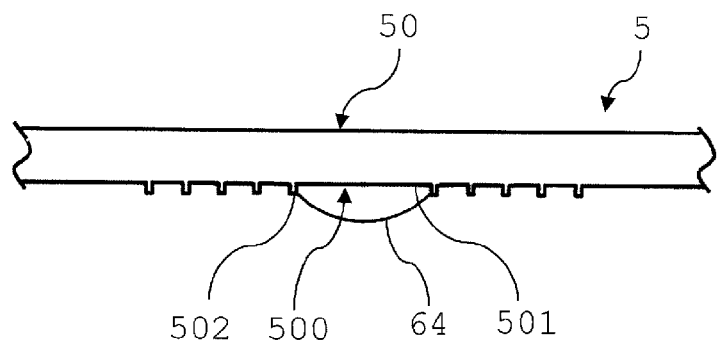
FIG. 10 shows a cross-sectional view of a third embodiment of the hanging droplet plate according to the invention, the droplet compartment containing a droplet.

FIG. 10-FIG. 14 show a single droplet compartment 50 of a third embodiment of a hanging droplet plate 5 according to the invention. This embodiment of the hanging droplet plate 5 is different from the first and second embodiment described in detail above in that it the compartment 50 does not comprise the microfluidic barriers in a stepped configuration but rather the microfluidic barriers in the form of circumferential rims are arranged on a plane lower surface of the plate 5. While the compartment 50 comprises again a closed bottom 500, the cavity 501 is bounded by a first circumferential rim 502 surrounding cavity 501 and protruding from the lower surface of plate 5. FIG. 10 shows a small liquid droplet 64 hanging down from compartment 50. Droplet 64 is retained in cavity 501 by the first circumferential rim 502 forming a microfluidic barrier.

Figure 11:
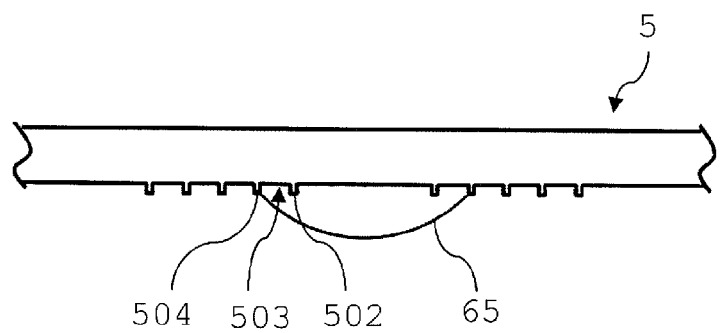
FIG. 11 shows the third embodiment of the hanging droplet plate according to the invention, with an additional droplet having been added.

FIG. 11 differs from FIG. 10 in that either another liquid droplet has been added to liquid droplet 64 to form a larger droplet 65 (also, a larger droplet 41 can be introduced into droplet compartment 50 as the first step). Larger droplet 65 is retained by a second circumferential rim 504 surrounding the first circumferential rim 302 with a wetting area 503 being arranged between first circumferential rim 502 and second circumferential rim 504. Again, second circumferential rim 504 acts as a microfluidic barrier preventing larger droplet 65 from spreading beyond rim 504.

Figure 12:
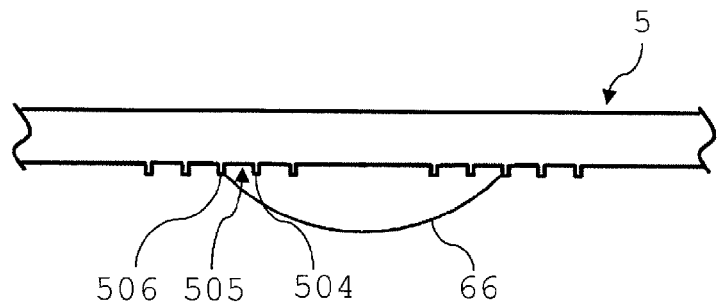
FIG. 12 shows the third embodiment of the hanging droplet plate according to the invention with another additional droplet having been added.

FIG. 12 shows a still larger droplet 66 which is retained by a third circumferential rim 506 that surrounds second circumferential rim 504 with a further wettable area 505 being arranged between second circumferential rim 604 and third circumferential rim 506. Third circumferential rim 506 again acts as a microfluidic barrier to prevent droplet 66 from spreading beyond rim 506.

Figure 13:
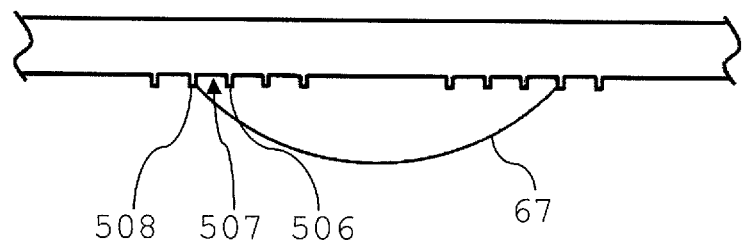
FIG. 13 shows the third embodiment of the hanging droplet plate according to the invention with still another additional droplet having been added.

FIG. 13 shows a yet larger droplet 67 which is retained by a fourth circumferential rim 508 that surrounds third circumferential rim 506 with a yet further wettable area 507 being arranged between third circumferential rim 506 and fourth circumferential rim 508. Fourth circumferential rim 508 again acts a microfluidic barrier to prevent the yet larger droplet 67 from spreading beyond rim 508.

Figure 14:
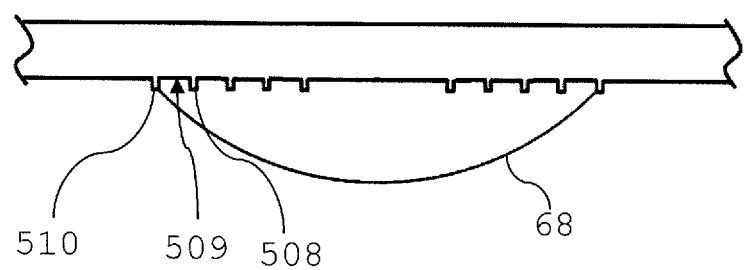
FIG. 14 shows the fourth embodiment of the hanging droplet plate according to the invention with yet another additional droplet having been added.

Finally, FIG. 14 shows an even larger droplet 68 which is retained by a fifth circumferential rim 510 that surrounds fourth circumferential rim 508 with another wettable area 509 being arranged between fourth circumferential rim 508 and fifth circumferential rim 510. In the same manner as described above, fifth circumferential rim 510 acts as a microfluidic barrier to prevent the even larger droplet 68 from spreading beyond rim 510.

Figure 15:
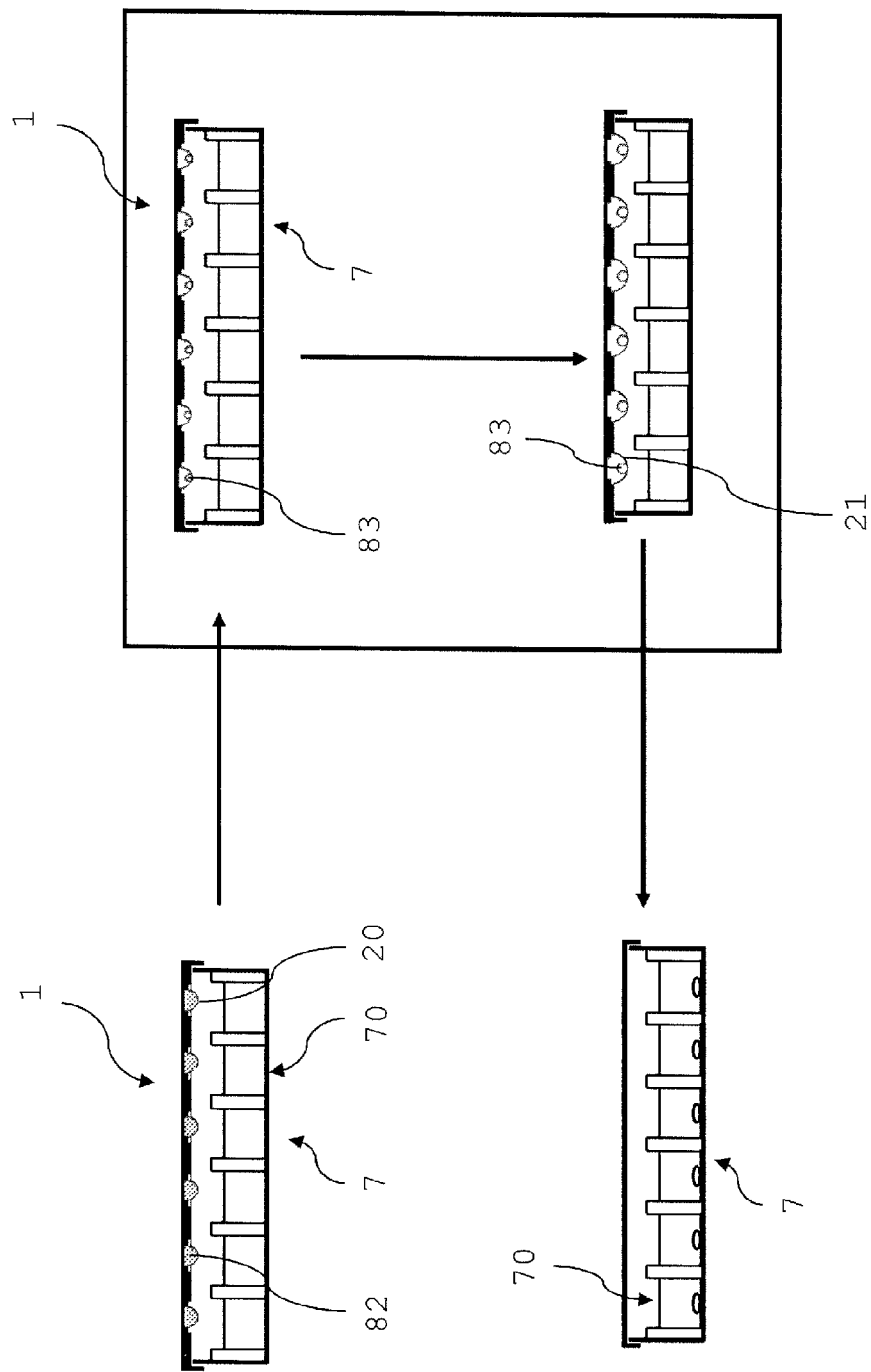
FIG. 15 shows an embodiment of an embryonic stems cell assay in which a hanging droplet plate according to the invention is used.
Figure 21:
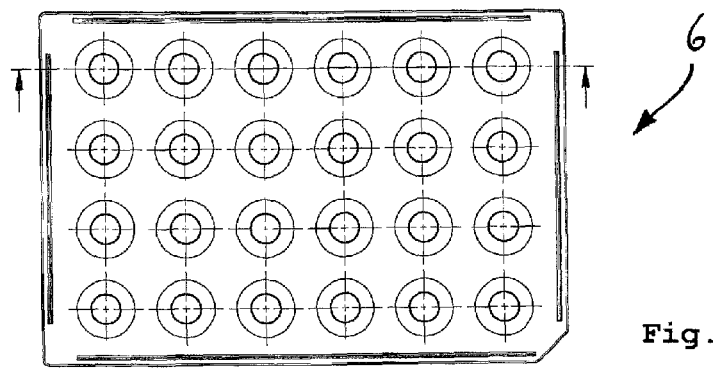
FIG. 21 shows a top view of the 24-well hanging droplet plate with the wells of FIG. 16 being inserted into the holes of the plate of FIG. 18.
Figure 22:
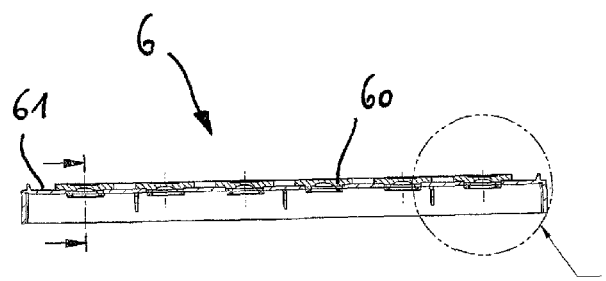
FIG. 22 shows a cross-section through the 24-well hanging droplet plate of FIG. 21.
Figure 24:
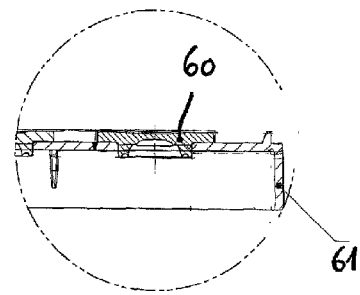
FIG. 24 shows a detail of the cross-sectional view of FIG. 22 including one well inserted into one hole.
Figure 23:
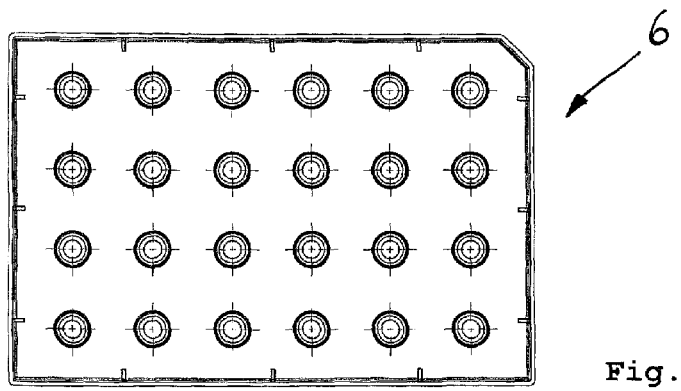
FIG. 23 shows a bottom view of the 24-well hanging droplet plate of FIG. 21.

In FIG. 15 an embodiment of an embryonic stem cell assay is shown representing an embodiment of the method according to the invention in which any of the above-described embodiments of the hanging droplet plate according to the invention can be used. For the following description of the assay it is assumed that the first embodiment of the hanging droplet plate 1 according to the invention is used. In this embodiment of the assay the toxicity of a substance to embryoid bodies is tested. For that purpose, a predetermined number of liquid droplets is introduced into a corresponding number of droplet compartments or wells. Each droplet contains a predetermined volume of the substance to be tested as well as a liquid culture medium as well as a plurality of stem cells 82. In case of the first embodiment of the hanging droplet plate 1 twenty-four droplets 20 may be introduced into the corresponding wells 10 while plate 1 is in the reinverted position (see FIG. 4). After the droplets 20 have been introduced into the wells 10, plate 1 is inverted and assembled with a further plate 7 having a corresponding number of wells 70 which are arranged opposite to the wells 10 of hanging droplet plate 1 so as to form a closed assembly. Wells 70 may contain culture medium, too. The assembly so formed may be so that the droplets 20 hang down from the wells 10 as this has been explained in detail above. The so formed assembly (see FIG.

15, top left) is incubated for a predetermined time interval, e.g. for three days. During this incubation period the stems cells 82 contained in the respective droplets settle down and form a three-dimensional embryoid body 83 (more generally a three-dimensional cellular aggregate) in the respective droplet 20 at the apex of the droplet, i.e. at the lowermost point of droplet 20 (see FIG. 15, top right).

After the first incubation period it may be necessary to supply additional liquid culture medium to the droplet 20 to promote additional growing of the embryoid bodies 83. For that purpose, the assembly is re-opened and the plate 1 is re-inverted. In this re-inverted position, additional liquid culture medium is supplied to the respective droplets 20 in the respective wells 10 to form larger droplets 21. Once the additional liquid culture medium has been supplied to form the larger droplets 21, plate 1 is inverted again and reassembled with further plate 7 (the wells 70 of which may also contain fresh liquid culture medium). The so formed assembly is incubated for a further predetermined time interval, e.g. for two days, to allow further growing of the embryoid bodies.

After the further incubation period the embryoid bodies 83 may be transferred into the wells 70 of plate 7 (receiving plate) by centrifugation, which can be done with a centrifugation device well-known in the art. After the embryoid bodies 83 have been centrifugated into the wells 70 of plate 7 containing liquid culture medium, the assembly may be incubated for another predetermined time interval, e.g. for five to seven days. The embryoid bodies 83 settle down to the plane bottoms of the respective wells 70 of plate 7.

Subsequent to this incubation period the assembly can be re-opened and the cellular aggregates can be examined as to whether the substance to be tested is toxic to cells. While various types of analyses are contemplated, one type of analysis is to analyze the cellular aggregates with the aid of a microscope. Since the cellular aggregates rest on the plane bottoms of the wells of plate 7, microscopic analysis is possible. For example, the cellular aggregates may be examined as to whether they contain myocardial cells, since this type of cells can be easily identified under the microscope, because these cells contract and expand (they beat).

The afore-described transfer of the embryoid bodies or three-dimensional cellular aggregates to the wells 70 of the further plate 7 through centrifugation is optional. Alternatively, the assembly can be re-opened and the plate 1 can be mounted to a centrifuge in a manner such that upon centrifugation the embryoid bodies or the cellular three-dimensional cellular aggregates are moved from the apex of the droplet towards the bottom 101 of well 10 (see FIG. 6). Subsequently, the embryoid bodies can be analyzed in the wells 10 of the plate with the aid of the microscope since they are arranged on the bottom 101 of well 10 which forms a stable background for the microscopic analysis.

FIG. 16-FIG. 24 show a further embodiment of the hanging droplet plate 6 (FIG. 21-FIG. 23) according to the invention. This embodiment comprises separately manufactured wells 60 (see FIG. 16 and FIG. 17) which can be press-fitted into holes 610 of a separately manufactured plate 61 (see FIG. 18-FIG. 20). As can be seen from the cross-sectional view of separately manufactured well 60 shown in FIG. 17, well 60 comprises first circumferential rim 602, second circumferential rim 604 and third circumferential rim 606. The structures and functions of the well and of the first, second and third circumferential rims have already been described in detail with the aid of FIG. 7, FIG. 8 and FIG. 9 and, therefore, it is referred to these parts of the description above. In the embodiment shown, wells 60 are press-fitted into holes 610 of plate 61 from that side of plate 61 forming the outer surface 611 of the plate 61. Once all wells 60 are press-fitted into holes 610 they are fixedly attached to plate 61 and formation of hanging droplet plate 6 is complete (FIG. 21-FIG. 24).

Alternatively, it is conceivable that the separately manufacture wells 60 are attached to the inner surface 612 of plate 61 (for example by ultrasonic welding or by gluing). In this case, plate 61 may not comprise holes. However, the locations where the ultrasonic welding or gluing of the wells 60 to the inner surface 612 of plate 61 has occurred may be visible and may make the microscopic analysis of the contents of the wells more difficult. Press-fitting of the wells 60 into the holes 610 of plate 61 is therefore preferred.

FIG. 25 and FIG. 26 show an embodiment of a further plate 8 which comprises a number of wells 80 corresponding to the number of wells 60 of hanging droplet plate 6. Also, wells 80 of further plate 8 are arranged in a manner corresponding to the arrangement of the wells 60 of hanging droplet plate 6.

As can be seen in FIG. 27 and FIG. 28, hanging droplet plate 6 can be mounted in a stacked manner onto further plate 8 in a manner such that each well 60 of hanging droplet plate 6 is arranged above a corresponding well 80 of further plate 8. One purpose of such assembly has already been described in detail with respect to FIG. 15 and, therefore, it is referred to these parts of the description above.

With the aid of FIG. 16-FIG. 28 only 24-well plates or assemblies of 24-well plates are described, however, similar considerations are applicable to 96-well plates, as will become clear in the following.

FIG. 29-FIG. 38 show yet a further embodiment of the hanging droplet plate 9 (FIG. 35-FIG. 37) according to the invention which is embodied as a 96-well hanging droplet plate. Similar to the 24-well embodiment, the 96-well embodiment comprises separately manufactured wells 90 (see FIG. 29-FIG. 31) which can be press-fitted into holes 910 of a separately manufactured plate 91 (see FIG. 32-FIG. 34). As can be seen from the cross-sectional views of separately manufactured well 90 shown in FIG. 30 and FIG. 31, well 90 comprises first circumferential rim 902, second circumferential rim 904 and third circumferential rim 906. The structures and functions of the well and of the first, second and third circumferential rims have already been described in detail with the aid of FIG. 7, FIG. 8 and FIG. 9 and, therefore, it is referred to these parts of the description above. In the embodiment shown, wells 90 are press-fitted into holes 910 of plate 91 from that side of plate 91 forming the outer surface 911 of the plate 91. Once all wells 90 are press-fitted into holes 910 they are fixedly attached to plate 91 and formation of hanging droplet plate 9 is complete (FIG. 35-FIG. 38).

FIG. 39-FIG. 41 show an embodiment of a further plate 92 which comprises a number of wells 920 corresponding to the number of wells 90 of hanging droplet plate 9. Also, wells 920 of further plate 92 are arranged in a manner corresponding to the arrangement of the wells 90 of hanging droplet plate 9.

As can be seen in FIG. 41, hanging droplet plate 9 can be mounted in a stacked manner onto further plate 92 in a manner such that each well 90 of hanging droplet plate 9 is arranged above a corresponding well 920 of further plate 92.

It goes without saying that the afore-described embodiments are only one examples of various applications of the method, hanging droplet plate and hanging droplet plate according to the invention, so that they are not intended to limit the invention thereto. Rather, the scope of protection is intended to be defined by the appended claims.

The invention claimed is:

1. A hanging droplet plate comprising:
   a predetermined number of droplet compartments each being capable of receiving a droplet of a liquid, each droplet compartment having a cavity and a circumferential microfluidic wetting barrier surrounding the cavity such that a droplet is prevented from spreading beyond the circumferential microfluidic wetting barrier, wherein each droplet compartment comprises a separate and distinct closed bottom within the circumference of the circumferential microfluidic wetting barrier and at least one additional circumferential microfluidic wetting barrier, each at least one additional circumferential microfluidic wetting barrier surrounding a preceding circumferential microfluidic wetting barrier, with a wettable area being arranged between two adjacently arranged microfluidic wetting barriers.

2. The hanging droplet plate according to claim 1, wherein each of the droplet compartments comprise a well.

3. The hanging droplet plate according to claim 1, wherein the circumferential microfluidic wetting barrier comprises a circumferential edge, the at least one additional circumferential microfluidic wetting barrier comprises at least one additional circumferential edge, each at least one additional circumferential edge being arranged to surround a preceding circumferential edge, with the wettable area being arranged between two adjacently arranged circumferential edges.

4. The hanging droplet plate according to claim 3, wherein two adjacent circumferential edges are arranged in a stepped manner.

5. The hanging droplet plate according to claim 1, wherein the circumferential microfluidic wetting barrier comprises a circumferential rim, the at least one additional microfluidic wetting barrier comprises an additional circumferential rim, each additional circumferential rim surrounding a preceding circumferential rim with the wettable area being arranged between two adjacently arranged circumferential rims.

6. The hanging droplet plate according to claim 5, wherein the adjacently arranged circumferential rims are arranged in a stepped manner.

7. The hanging droplet plate according to claim 2, wherein the hanging droplet plate is made of a separately manufactured plate having a predetermined number of holes therein and of a corresponding predetermined number of separately manufactured wells forming the droplet compartments, with each separately manufactured well being press-fitted into a respective hole of the separately manufactured plate.

8. The hanging droplet plate according to claim 7, wherein the separately manufactured wells are press-fitted into the holes from the side of the plate forming the outer surface of the plate.

9. The hanging droplet plate according to claim 7, comprising 24 wells, 96 wells or 384 wells.

10. The hanging droplet plate according to claim 5, wherein the circumferential rims are arranged on a plane surface.

11. A hanging droplet plate assembly, comprising:
a hanging droplet plate according to claim 1, the plate having a predetermined number of droplet compartments; and
a receiving plate having a number of wells corresponding to the predetermined number of droplet compartments of the hanging droplet plate, the hanging droplet plate and the receiving plate being assembled in a manner such that in the assembled state the wells of the receiving plate are aligned with the droplet compartments of the hanging droplet plate.

12. A method of testing a substance for its toxicity to cells, comprising:
introducing a predetermined number of liquid droplets into a corresponding number of droplet compartments of a hanging droplet plate, each droplet containing a predetermined volume of the substance to be tested and of a liquid culture medium as well as a plurality of cells;
inverting and incubating the hanging droplet plate for a predetermined time interval with the hanging droplet plate carrying the droplets in a manner such that they hang down from the respective droplet compartments to allow the cells to form three-dimensional cellular aggregates in the respective droplets;
supplying additional liquid culture medium to the droplets in the respective droplet compartments to promote additional growing of the three-dimensional cellular aggregates; and
analyzing the three-dimensional cellular aggregates in order to assess whether the substance to be tested is toxic to the three-dimensional cellular aggregates, wherein a hanging droplet plate according to any one of the preceding claims is used; and wherein supplying the additional liquid culture medium step is performed by re-inverting the hanging droplet plate, adding a droplet of the additional liquid culture medium to the respective droplets containing the three-dimensional cellular aggregates so as to form respective larger droplets in the respective droplet compartments, and then inverting the hanging droplet plate again to allow the three-dimensional cellular aggregates to grow in the respective larger droplets hanging down from the droplet compartments.

13. The method according to claim 12, further comprising:
transferring the grown three-dimensional cellular aggregates from the droplet compartments of the hanging droplet plate into a corresponding number of wells of a receiving plate;
incubating the receiving plate with the wells containing the three-dimensional cellular aggregates for a further predetermined time interval; and
after incubation, analyzing the three-dimensional cellular aggregates in order to assess whether the substance to be tested is toxic to the three-dimensional cellular aggregates.

14. The method according to claim 13, wherein the transferring step is performed by assembling the hanging droplet plate and the receiving plate in a manner such that the respective wells of the receiving plate are arranged opposite to the respective droplet compartments of the hanging droplet plate, and by subsequent centrifugation of the assembled plates.

15. The method according to claim 13, wherein the cells are embryonic stem cells and the three-dimensional cellular aggregates are embryoid bodies, and wherein the step of analyzing the three dimensional cellular aggregates to assess whether the substance to be tested is toxic to the three-dimensional cellular aggregates is performed by analyzing whether the embryoid bodies contain myocardial cells.

* * * * *